US010987151B2

(12) United States Patent
Ho et al.

(10) Patent No.: US 10,987,151 B2
(45) Date of Patent: Apr. 27, 2021

(54) PLASMA-SURGICAL APPARATUS COMPRISING A SPACER

(71) Applicant: Ovesco Endoscopy AG, Tubingen (DE)

(72) Inventors: Chi-Nghia Ho, Tubingen (DE); Gunnar Anhock, Tubingen (DE); Gabor Conrad, Tubingen (DE); Marc O. Schurr, Tubingen (DE); Thomas Gottwald, Tubingen (DE)

(73) Assignee: Ovesco Endoscopy AG

( * ) Notice: Subject to any disclaimer, the term of this patent is extended or adjusted under 35 U.S.C. 154(b) by 566 days.

(21) Appl. No.: 14/934,006

(22) Filed: Nov. 5, 2015

(65) Prior Publication Data
US 2016/0128755 A1 May 12, 2016

(30) Foreign Application Priority Data
Nov. 7, 2014 (DE) ...................... 10 2014 116 523.6

(51) Int. Cl.
*A61B 18/04* (2006.01)
*A61B 18/00* (2006.01)
*A61B 18/12* (2006.01)

(52) U.S. Cl.
CPC .. *A61B 18/042* (2013.01); *A61B 2018/00083* (2013.01); *A61B 2018/00178* (2013.01);
(Continued)

(58) Field of Classification Search
CPC ................. A61B 18/042; A61B 18/14; A61B 2018/00607; A61B 2018/00577;
(Continued)

(56) References Cited
U.S. PATENT DOCUMENTS 5,720,745 A * 2/1998 Farin ................. A61B 18/042
128/898
6,063,084 A * 5/2000 Farin ................. A61B 18/1492
606/40
(Continued)

FOREIGN PATENT DOCUMENTS

DE         9117111 U1    11/1995
DE   21 2006 000 066 U1    9/2008
(Continued)

OTHER PUBLICATIONS

English translation of Office Action in parallel Japanese application No. 2015-218342 dated Jul. 14, 2017.
(Continued)

*Primary Examiner* — Michael F Peffley
(74) *Attorney, Agent, or Firm* — RatnerPrestia

(57) ABSTRACT

The disclosure relates to a spacer in the form of an attachment (15) to be mounted to an endoscope (1), said attachment being formed like a cap, enclosing a spatial volume (16) and being made of an insulating material. The attachment (15) is further equipped with a mounting device/adapter (6) designed to be coupled to a distal end of the endoscope (1). The attachment (15) comprises an area (11) designed to be in contact with a target tissue and further forms an aperture (12) enclosing a surface area (12*a*). Within the spatial volume, there is arranged an electrode (9) comprising a distal (9*b*) and a proximal (9*a*) end, the distal (9*b*) end of the electrode (9) having a predetermined minimum distance to the closest point of the surface area (12*a*).

15 Claims, 7 Drawing Sheets

(52) U.S. Cl.
CPC .............. *A61B 2018/00577* (2013.01); *A61B 2018/00791* (2013.01); *A61B 2018/1213* (2013.01)

(58) Field of Classification Search
CPC ........... A61B 2018/00583; A61B 2018/00791; A61B 2018/1213; A61B 2018/00083; A61B 2018/00178; A61N 1/44
See application file for complete search history.

(56) References Cited

U.S. PATENT DOCUMENTS

| | | | | |
|---|---|---|---|---|
| 6,958,063 | B1 * | 10/2005 | Soll | A61B 18/042 606/32 |
| 7,361,175 | B2 * | 4/2008 | Suslov | A61B 18/042 606/49 |
| 7,445,619 | B2 * | 11/2008 | Auge, II | A61B 17/88 606/41 |
| 9,901,394 | B2 * | 2/2018 | Shadduck | A61B 18/148 |
| 2006/0189976 | A1 | 8/2006 | Karni et al. | |
| 2007/0106288 | A1 * | 5/2007 | Woloszko | A61B 18/148 606/41 |
| 2011/0077642 | A1 | 3/2011 | Farin | |
| 2011/0301412 | A1 * | 12/2011 | Cho | A61B 1/00091 600/104 |
| 2012/0041437 | A1 | 2/2012 | Truckai | |
| 2013/0090644 | A1 * | 4/2013 | Williams | A61B 18/042 606/40 |

FOREIGN PATENT DOCUMENTS

| | | | |
|---|---|---|---|
| DE | 102009002278 A1 | 10/2010 | |
| DE | 10 2008 004 843 B4 | 9/2012 | |
| DE | 2008004843 * | 9/2012 | ............. A61B 18/12 |
| DE | 102008004843 B4 | 9/2012 | |
| GB | 2495400 A | 4/2013 | |
| JP | 4-10328 B2 | 2/1992 | |
| JP | 06-063060 | 3/1994 | |
| JP | 2011-506010 A | 3/2011 | |
| JP | 2012-506297 A | 3/2012 | |
| WO | 2006084316 A1 | 8/2006 | |

OTHER PUBLICATIONS

Search Report in German Application No. DE 10 2014 116 253.6 dated Oct. 5, 2015, issued by the German Patent and Trademark Office, 10 pages.

European Patent Office, European Search Report, dated Apr. 7, 2016, 6 pages.

Notification of Reasons for Rejection in parallel Japanese Application 2015-218342, dated May 15, 2018, with English Translation.

* cited by examiner

PLASMA-SURGICAL APPARATUS COMPRISING A SPACER

Embodiments of the invention relate to an attachment or (tissue) spacer of a plasma-surgical apparatus as well as to a plasma-surgical apparatus for treating a target tissue/body tissue with a plasma arc, the plasma-surgical apparatus using the attachment or (tissue) spacer, embodiments of which are described herein.

BACKGROUND OF THE INVENTION

Plasma-surgical methods as well as plasma applicators and such appliances/devices for using these methods are basically known. For more than 50 years, a plasma-surgical method which is known as fulguration or spray coagulation is used in surgical operations, in particular for thermal hemostasis.

In this process, a plasma is exclusively produced in air, i.e. mainly oxygen plasma and nitrogen plasma are generated. As is well known, both plasma species are chemically very reactive and bring about carbonization effects, pyrolysis effects and hence also vaporization of tissue as well as smoke on the tissue surface. These unintentional side effects of the fulguration or spray coagulation disturb or impede the application of this plasma-surgical method, in particular in endoscopic operations. This is why the gas has been generally replaced by a noble gas, in particular argon, to avoid these disadvantages.

PRIOR ART

DE 10 2008 004 843 B4, for instance, discloses a plasma treatment apparatus which is used for flexible endoscopy.

Due to its construction, said apparatus is capable of carrying out a plasma-surgical treatment within a human body. With this known surgical apparatus, a probe or a catheter is placed within an endoscope or is inserted in its working channel, the latter delivering the electrical energy from a high-frequency current/voltage source or a generator to an electrode on the distal end of the probe/catheter via a connection line placed in the interior of the probe/catheter.

The text below will only make reference to the catheter. The afore-mentioned probe is analog in its meaning.

At the mentioned electrode, a plasma arc forms between the tip of the electrode and a body tissue/target tissue in the direct vicinity by means of the introduced electrical energy. The electrode is situated on the distal end of the probe and hence projects in distal direction beyond the endoscope and out of its working channel.

According to DE 10 2008 004 843 B4, a resistive element, explicitly a capacitive resistive element, is additionally arranged between the distal end of the connection line placed in the catheter and the proximal end of the electrode and hence is positioned immediately upstream of the electrode. Said resistive element has the function to limit the power which is delivered by the current/voltage source (in the following referred to as a "generator") and flows through the target tissue and consequently through the human body. Said afore-mentioned arrangement ensures that the resistive element is positioned to be as close as possible to the proximal end of the electrode. Said proximity prevents an excessively high influence of the stray capacitances (occurring in the system due to line portions between the resistive element and the electrode) on the voltage drop between the electrode tip and the target tissue. Thus, the current flowing through the target tissue is limited in a defined or definable manner mainly by the resistor provided between the connection line and the electrode.

One problem arising in all treatment apparatuses which use a plasma arc for treating tissue also arises with the surgical instrument according to DE 10 2008 004 843 B4:

The electric arc is formed in a gaseous atmosphere, preferably in a noble gas atmosphere such as argon. Here, the gaseous atmosphere is ionized by the high field strength occurring on the pointed distal end of the electrode. The gas is rendered electrically conductive and now constitutes an electrically conductive plasma. This conductive gas or plasma allows an electric current to flow between the target tissue (being in electrical connection with a neutral electrode) and the tip of the electrode. An electric arc is created within the electrically conductive plasma and allows the surgeon to treat (coagulate, cut) the respective target tissue.

In order to ignite this electric arc for the first time, the treating surgeon has to position the electrode with such a small distance to the target tissue that the field strength on the electrode tip will become so large that the electric arc is ignited. The distance is in the range of approximately 2 mm between the tip of the electrode (i.e. its distal end) and the patient-side target tissue. As soon as the electric arc is ignited in the plasma, the electric arc continues to burn even if the distance between the target tissue and the electrode changes (within limits).

The afore-mentioned problem is of minor importance in the open plasma surgery, i.e. if it is not carried out within the human body. The circumstances are more problematic if the target tissue, which is to be treated with plasma-based surgery, lies within the human body.

For monitoring the area of intervention or for visually checking the work, a camera is generally used which is also located in the endoscope or in a functional channel provided in the endoscope or is inserted in some other way into the patient for monitoring the target tissue to be treated. The handling of the plasma-surgical apparatuses is carried out in remote fashion, i.e. from outside the body. This prevents a direct visual or haptic feedback to the surgeon which has to fully rely on the image of the treatment-/operation zone delivered by the camera.

As the entire tissue of the body of the patient is at the potential of the neutral electrode connected to him (which electrode is required to get a closed circuit in the monopolar surgery used here), it can not be precluded with the open (monopolar) electrode of the plasma-surgical apparatus of the prior art that a tissue which is not supposed to be treated is closer to the electrode than the desired target tissue. In this case, the electric arc ignites on said closer tissue, as the electric current according to electrotechnical laws always looks for the line of least resistance.

Due to these "fault ignitions" or if the plasma arc upon igniting is held too close to the target tissue and also too long, undesired effects may arise on the tissue. Depending on the treatment current, it may happen for instance that the tissue in more deeper regions is unnecessarily injured by the intervention or that an excessively large surface area is impaired or an undesired coagulation, burn etc. occurs.

The open electrode in DE 10 2008 004 843 B4 further requires that the treating surgeon keeps the distance to the target tissue as constant as possible, as otherwise—as with the initial ignition—the electric arc may jump over to a tissue which is not intended for treating. Here, the current through the electric arc does not only depend on the resistive element situated upstream of the electrode, but also on the distance between the electrode and the target tissue. The smaller the distance, the higher the treatment current and hence the penetration depth.

What is more, the resistive element used according to DE 10 2008 004 843 B4 is quite complex. In order to place the resistive element as far forward as needed, it must be of very small size in order to be able to be built in the probe and pushed through the working channel of an endoscope. Standardized industrial parts do not allow to realize this with probe diameters of around 2.5 mm. Therefore, said document DE 10 2008 004 843 B4 suggests a special construction in which the probe line and parts of the electrode itself constitute the resistive element. This is indeed feasible in theory, but in particular in practice the required resistance values can be realized only with difficulty in this way, as constant values of the resistive element are crucial.

Any changes in the capacity have a negative impact on the work with the instrument. This is why there is the desire to further develop the technology in such a manner that it is possible to use standardized parts.

BRIEF DESCRIPTION OF THE INVENTION

The invention is based on the object to further develop a plasma-surgical apparatus such that, on the one hand, the plasma arc is prevented from igniting in the form of parasitic arcs on healthy body tissue not intended for being treated. According to a further aspect of the present application, the treating surgeon shall have the opportunity to reliably ignite the electric arc at any time. This is to be ensured even under such difficult conditions if the treatment site is within the human body and the plasma applicator has to be operated from outside. Finally, a preferred aim of the present invention is to provide a plasma-surgical apparatus in which components which are essentially optimized in their function can be used in particular for the resistive element and/or the electrode; nevertheless, said apparatus shall be capable of being pushed through the working channel of an endoscope with standardized diameter (approximately 5 mm) without any problems.

The object is achieved by a spacer and a surgical instrument according to the independent claims 1 and 11, respectively. Further advantageous developments are the subject-matter of the sub-claims.

The basic idea of the present invention is to provide a spacer (as a separate element of the surgical apparatus/instrument according to the invention) which is adapted to be selectively mounted as an auxiliary part to the distal end of a feeding device e.g. of the endoscope type. In the first place, the spacer or attachment has the function to keep a defined distance between the distal end of the feeding device and a patient-side target tissue, if the spacer rests on the target tissue in a contact area of the spacer provided for this purpose.

Further, the electrode realized with a connection to which an electrical cable can be connected which is pushed through the working channel of the feeding device may already be installed in the spacer. In this case, the shape of the electrode can be optimized corresponding to its function, as the electrode itself does not have to be pushed through the working channel. As an alternative to this, the spacer may also be provided with an electrode positioning means where an electrode pushed through the working channel of the feeding device positions itself (automatically) and in this way adopts the correct position relative to the contact portion of the spacer.

Finally, the spacer may also take the function of supporting a resistive element. In this case, the electrode and the resistor known per se from prior art can be mounted within the spacer, the resistor in this case being provided with the connection for the cable to be pushed through the working channel of the feeding device.

In more specific terms, a sort of attachment for a feeding device (endoscope) is suggested according to the invention, with the aid of which a surgical instrument for treating a target tissue/body tissue with a plasma arc (monopolar electric arc design) can be inserted, the attachment being affixed or being able to be affixed on the distal end of the feeding device (of the endoscope). The attachment is affixed or can be affixed on the feeding device (on the endoscope) or on its (endoscope) head and is designed to be cap-shaped on its distal portion. The surface (circumferential wall) of the attachment which is cap-shaped on the whole or its attachment wall encloses a spatial volume to be filled with a gas, preferably a noble gas such as argon.

The attachment may be realized preferably in two pieces and to this end comprise a first cap-shaped piece on the distal end portion. Advantageously, the distal end of the attachment (the first cap-shaped piece) is rounded towards outside or bulged in a convex shape. Further, the attachment may comprise a second piece on its proximal end portion. This second piece on the proximal end portion serves as a mounting device/an adapter and is fastened to the distal end of the feeding device (of the endoscope) or is designed to be capable of being fastened thereto.

In a preferred exemplary embodiment, both mentioned pieces of the attachment are formed separate from each other and can be connected (plugged, latched etc.) to each other. As an alternative, it is also possible to design the two mentioned pieces quasi as functional portions integrally made of one material. It is preferred that the attachment consists of an electrically non-conductive material, in other words of an electrically insulating material such as a plastic or ceramic material.

An electrode is arranged within the spatial volume of the attachment or can be arranged therein. The electrode has a distal end and a proximal end. It is usually the proximal end of the electrode which is connected to or can be connected to an energy source. The energy source, alternatively also a generator or a current/voltage source, provides the energy for the formation of a plasma arc and thus allows the treatment of the target tissue.

Furthermore, the attachment may advantageously comprise an area/portion which is designed/provided to rest on the target tissue/body tissue of a patient. This area can hence come into contact with the target tissue and may comprise a treatment aperture or treatment window defining a surface area with a specific size corresponding to the intended treatment zone. The target tissue to be treated is therefore exclusively in the area of the aperture/of the window, in particular in case the aperture/window rests on the target tissue. Stated in other words, the aperture/window has the function to expose preferably the target tissue enabled to be treated.

This offers the basic opportunity to optimize the surgical instrument inserted in the feeding device by exchanging/selecting the attachments having different aperture sizes and/or spatial volumes for different treatments and target tissues. It is preferred that this contact area of the attachment including the aperture/window is of planar design.

The mounting device/adapter (or adapter portion) of the attachment according to the invention is configured preferably in the nature of a sleeve, hose or bushing (or also a simple adhesive tape) and has a proximal connection aperture adapted to be able to be connected to the endoscope (preferably slipped/put over it). A line extending through the central point of this connection aperture so as to be perpendicular to the plane of the connection aperture (corresponds approximately to the center line of the bushing) represents a longitudinal axis of the entire endoscope attachment. This longitudinal axis may extend axially or parallel to the longitudinal axis of the endoscope.

According to a preferred exemplary embodiment, the treatment aperture/treatment window is oriented inclined at an angle of unequal to 90° and unequal to 0°, preferably of between 30° to 60° relative to the longitudinal axis. This means that the intended area of contact between the endoscope attachment and the target tissue is not perpendicular to the axis of the instrument/endoscope, but is oriented at a specific, preferably acute inclination angle relative to the axis of the instrument/endoscope in distal direction. It is preferred that the inclination angle is selected such that an optical system or such imaging apparatus of the feeding device/of the endoscope accommodated in a functional channel of the endoscope has a preferably free, unobstructed view on the target tissue exposed through the treatment aperture/window, without being limited by the electrode protruding into the enclosed spatial volume.

The distal end of the electrode may have a predetermined minimum distance to a specific point within the mentioned surface area, preferably to the closest point and further preferred to the central point and hence may also have a predetermined minimum distance to the target tissue below the treatment aperture, being fixedly defined by the shape of the attachment. This even applies if the mentioned area of the attachment rests on the target tissue.

If the area of the attachment comprising the treatment aperture rests on the target tissue, the treating surgeon can be sure of keeping the correct treatment distance and a preferred minimum distance between the distal end of the electrode and the target tissue as long as the attachment has contact with the target tissue. With this, a preset energy level achieves a constant treatment depth and treatment intensity of the arising electric arc.

Moreover, the material of the attachment preferably possesses electrically insulating characteristics, as it is preferably made at least in part from a non-conductor such as a plastic material or ceramics. This is why the electric arc will always form between the electrode and the target tissue situated in the area of the aperture/window. A faulty formation of an electric arc (a parasitic electric arc) between the electrode and a tissue zone not to be treated cannot occur any longer. This means that the preferred cap-shaped configuration of the attachment guarantees that only the treatment tissue is acted upon with the electric arc through the treatment aperture, whereas neighboring tissue is shielded by the electrically insulating attachment wall. This offers the treating surgeon a higher safety during use of the plasma-surgical apparatus.

It is conceivable to use the attachment according to the invention not only with surgical apparatuses/instruments which are applied in the endoscopic field. Also in the open plasma-based or high-frequency surgery, the attachment assists in keeping a defined distance for the ignition of the electric arc. In this case, the attachment could be mounted to a handle, for instance, to allow a handling outside the patient body.

The idea of the invention is not restricted to an attachment comprising the above constructional attributes. All attachment constructions which allow to keep a defined distance between an electrode and a target tissue during a plasma treatment and at the same time prevent parasitic arcs between the electrode and the surrounding target tissue are in the scope of the present invention. Thus, it is not absolutely necessary to realize the attachment with a rounded cap shape. It would also be possible in a simplified configuration to use a straight cylinder in which the electrode is mounted or which contains a positioning means for the electrode, whereby a predefined position of the electrode relative to the contact portion on the target tissue is achieved.

In a further embodiment, the proximal end of the electrode can be directly connected to a first end of a resistive element. This connection may be a suitable electrical connection such as a weld connection, a crimp connection, a soldered connection or an electrical plug contact.

The second end of the resistive element may be connected to an energy supply via a conductor which is preferably placed in a catheter. To this end, the second end of the resistive element may be connected or may be able to be connected to the electrical conductor in the catheter via a suitable electrical connection. This can be, for instance, a plug connection, a weld connection, a screw connection, a crimp connection or a soldered connection. An exceptional flexibility in changing the electrode and/or the resistor is ensured by a detachable electrical connection from the distal end of the catheter to the second end of the resistive element or also while bypassing the resistive element directly to the proximal end of the electrode, for instance by means of a suitable electrical plug connector or other detachable electrical connection means.

The resistive element itself may be constituted by one or more discrete components. The components may be integrated on a small board to an electronic assembly module. The components can be interconnected in parallel and/or series connection, depending on which resistance value is to be achieved with the components.

For limiting the current of the electric arc, the resistive element may be an ohmic resistor or a complex resistor such as a capacitor. It is preferred that commercially available capacitors are used for building up the resistive element.

The resistive element may be arranged within the attachment and advantageously within the volume of the attachment. A special construction in which the resistive element is patterned on the inner shape of the attachment, for example, is also conceivable. As an alternative, the resistive element may be fully enclosed by the material of the cap and hence may be an integral element of the cap or the attachment.

In that case, the resistive element may be integrated in the attachment such that when using an endoscope camera the field of vision of the camera is advantageously not impaired by the resistive element. The integration of the resistive element in the contact means between the catheter and the resistive element itself is possible with resistive elements with suitable electrical properties and an appropriate size.

In a further preferred embodiment, the endoscope for which the attachment is intended may have one or more functional channels. Functional channels are tubular cavities in an endoscope which allow to insert tools which have their diameter adapted to the endoscope channel (working channel) from outside the body up to an intervention site in the body of a patient.

For monitoring the working area and the target tissue to be treated, an endoscope camera can be arranged in a further functional channel of the endoscope, for example. As an alternative, the camera and an optional illumination system may be inherent parts of the endoscope.

A catheter may be arranged/inserted in the functional or working channel of the endoscope, with the option of arranging an electrical conductor within the catheter. The distal end of the catheter may comprise electrical contact means which are designed such and are suitable for being connected to an end of the resistive element or directly to the proximal end of the electrode. To this end, the resistive element and/or the electrode have matching electrical contact means/connections.

In case the resistive element for limiting the treatment current is already installed in the generator itself, the proximal end of the electrode arranged in the attachment can also be directly connected to the contact means on the distal end of the catheter.

In addition to the mentioned electrical conductor, the catheter may comprise a lumen through which a gas, preferably a noble gas, can be carried to the treatment site. During the treatment, the gas fills the internal volume of the attachment/cap which is enclosed by the cap or attachment. Due to the fact that the attachment or cap has a treatment aperture which only opens to the target tissue, the gas remains concentrated in the region of the treatment site to a somewhat better degree. As there is always a supply of fresh gas into the attachment chamber/the cap, the smoke or vapor which may be produced during the treatment with the plasma arc is specifically carried away from the treatment site via the aperture. With this, it is removed in an advantageous way also from the viewing area or from an area which is observed by an endoscope camera located in another working channel of the endoscope.

In a further advantageous way, the attachment of the surgical instrument/of the endoscope may comprise markings in the area of the treatment aperture. These markings may form a scale, for instance, which is arranged such that it allows to draw conclusions on the proportions of the target tissue which is to be treated and can be seen in the treatment aperture/in the treatment window.

These markings and said scale may be visible on the camera image or on an external monitor via an optical system or a camera which may also be additionally provided in another endoscope channel/functional channel.

The markings/the scale may be embedded in the material of the attachment or have a relief-like structure. They can also be printed on the material of the attachment.

In a further preferred embodiment, the attachment may be integrally formed from the cap and the mounting device/adapter. In case of a one-piece design, that part of the attachment which is connected or can be connected with the endoscope may be made of an elastic material.

The cap-shaped part of the attachment may consist of a comparably rigid and electrically insulating material. Advantageously, the material of the attachment may consist of a translucent material on the whole or in part.

A one-piece attachment comprising a torsionally rigid cap and a rubbery-elastic end/adapter to be mounted to an endoscope can be produced, for instance, with a 2-K technology in an injection molding method.

However, a two-piece configuration of the attachment is also possible and is preferred, too. If the attachment has a two-piece design, the cap-shaped part/the cap and the mounting device/adapter are two individual elements preferably made of different materials with different mechanical properties.

The mounting device/adapter serves to be fastened with its proximal end to the distal end of the feeding device/of the endoscope (by slipping it over said end). For this reason, it is advantageous if the mounting device/the adapter, which may also be referred to as a bushing or sleeve, consists of a rubbery-elastic material or a simple adhesive tape. With this, it can be slipped over or fastened to endoscopes of different diameters. The bushing may also consist of a non-elastic material. In this case, the bushing can be fastened in accordance with its dimensions only to that endoscope type which matches the diameter of the bushing.

At the other, distal end the bushing may be designed to be connected with a side of the cap. In the area where the bushing and the cap are connected with each other, the bushing as well as the cap may be equipped with corresponding connection means such as a bayonet lock or a screw connection. An adhesive connection is also conceivable. These connections between the bushing and the cap allow to use various caps for one and the same endoscope, as the bushing can remain on the endoscope. As an alternative, the entire attachment inclusive of the bushing and the cap can be exchanged.

If the resistive element and the electrode are part of the cap/of the attachment, an exchange of the cap/of the attachment allows to have influence on the treatment depth which depends on the values of the resistive element.

In a further advantageous way, the attachment may comprise, for monitoring the thermal conditions, a temperature measuring device such as an NTC resistor or any other suitable means for measuring an absolute temperature or a temperature change.

In addition, said means can be configured such that the values obtained in the course of the temperature measurement are also transmitted. The information on the temperature in the attachment can be transmitted, for example, via the electrical conductor of the catheter and delivered as an electronically processible information, e.g. by means of a multiplex method or the like. A wireless transmission by means of a suitable device in the attachment or in the endoscope is also possible. For visualizing, the temperature value can be displayed, for instance, in the camera picture of the endoscope camera. An external display on a dedicated apparatus is also conceivable.

DESCRIPTION OF THE FIGURES

The invention will be explained in more detail below on the basis of a particular exemplary embodiment with reference to the accompanying Figures in which:

In FIG. 1, there can be seen the essential components of a preferably minimally invasive plasma-surgical apparatus/instrument according to a preferred exemplary embodiment of the invention in exploded view. According to the present exemplary embodiment, the plasma-surgical apparatus/instrument is provided for being inserted in the working channel of a feeding device preferably in the form of an endoscope 1 which usually is realized so as to have several (in the present case four) functional/working channels 1a to 1d; in particular, the endoscope usually comprises only one working channel for the insertion of a medical tool and the remaining channels are provided, for example, for illumination purposes, for optical elements, for extraction, rinsing, etc.

Figure 1:
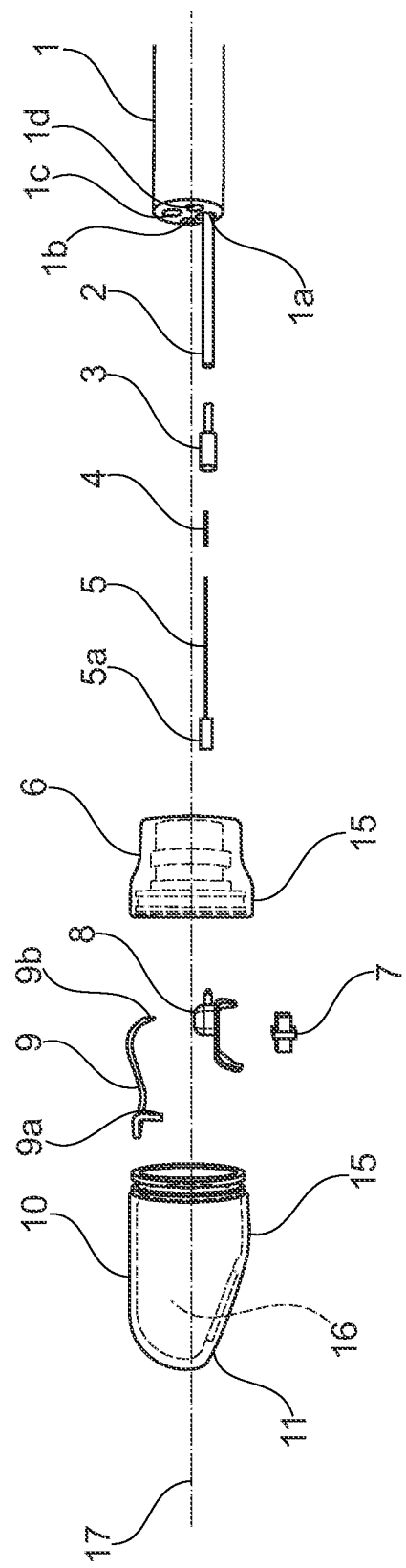
FIG. 1 shows the individual elements of a plasma-surgical instrument according to a preferred exemplary embodiment of the invention, in particular an attachment consisting of a cap-shaped first piece and a bushing or mounting device/adapter as the second piece for the selective fastening to a feeding device/an endoscope as well as the pieces located in the attachment such as the electrode, the resistive element and the connecting socket, with the catheter/electrical cable of the instrument being only indicated.

A catheter 2 (tool) of the surgical instrument according to the invention is placed in the working channel 1a of the endoscope 1 or is inserted/can be inserted therein. Among other things, the catheter 2 comprises electrical contact means (cable, wires, cable terminals) 3-5a which are required to deliver energy from a generator (not shown) to an electrode 9 on the distal end of the surgical instrument (endoscope 1). A tubular or sleeve-shaped mounting device/adapter 6 can be seen, having one axial side with a smaller diameter and one axial side with a larger diameter. The side with the smaller diameter, pointing toward the distal end of the endoscope 1, forms the side with which the mounting device/adapter 6, also referred to as a bushing, is fastened to the endoscope 1 in particular on its endoscope head. To this end, the side having the small diameter forms a preferably elastic hose portion with an essentially smooth inner wall, which can be attached to/put over the endoscope 1 in order to adhere thereon in a spring-elastic or frictional fashion. The side with the large diameter, likewise constituting an elastic hose portion, however, has an internally surrounding annular protrusion or bead.

An application cap 10 is mounted or can be mounted to the distal axial side of the bushing 6 having the large diameter. To this end, the application cap 10 has its external shape based on a thimble or cup comprising a rounded distal end portion and a sleeve-shaped proximal end portion whose external circumference is equipped with a latching groove. For the purpose of mounting the application cap 10 to the bushing 6, it is pulled over the sleeve-shaped proximal cap end portion, whereby the bushing-side bead latches in place in the cap-side latching groove in a form-locking manner. In this way, the application cap 10 can be mechanically connected to any standard endoscope via the elastic bushing 6 independently of the cap's size, diameter and/or shape.

At this point, it is to be emphasized again that the feeding device (endoscope) 1 is not part of the surgical instrument according to the invention, but merely serves as an insertion aid when inserting the surgical instrument into the interior of a patient. The surgical instrument itself consists of the catheter (with internal cable), the electrode (optionally with a resistor arranged immediately upstream thereof) which can be connected or is connected thereto and a spacer consisting of the application cap 10 as well as the mounting adapter 6.

In combination, the application cap 10 and the bushing 6 form the spacer/endoscope attachment 15 which in this preferred case consists of the two mentioned separate pieces 6, 10. In this way, the bushing 6 may consist as a whole e.g. of an elastic material and the cap 10 of a rigid/stiff material. As an alternative, the endoscope attachment 15 comprising the two functional portions may also be integrally made of one material.

Figure 2:
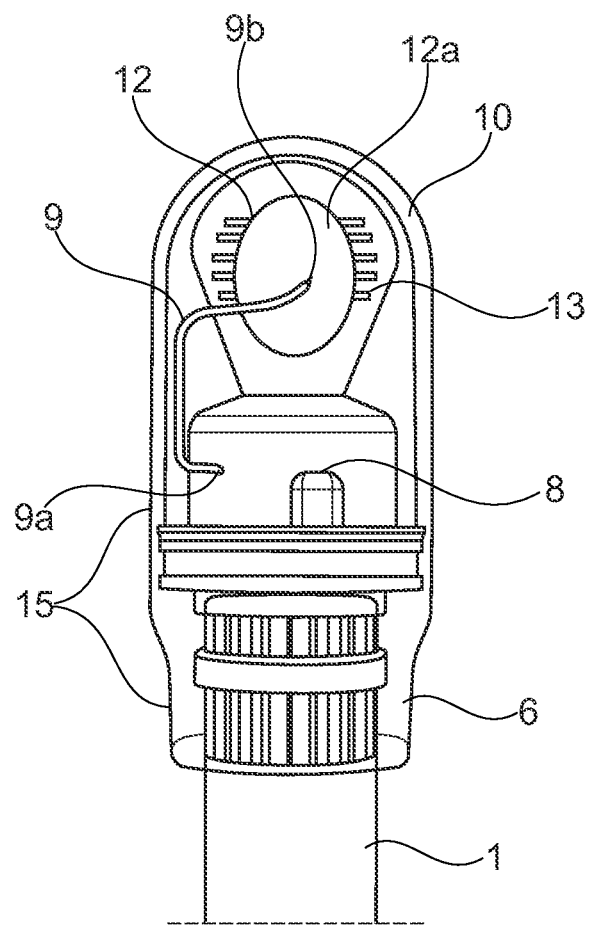
FIG. 2 shows the attachment of the plasma-surgical instrument comprising the mounting device/adapter provided on the endoscope and the electrode situated in the interior area of the attachment as well as a treatment aperture/window in the attachment.

According to FIGS. 1 and 2, the application cap 10 comprises a preferably flattened/planar (support) area 11 which is provided to come into contact with a target tissue of a patient. Assuming that the sleeve-shaped bushing 6 has a central/axial axis 17 which at the same time also forms the longitudinal axis of the application cap 10, said planar area 11 is situated to be off-center and inclined at an acute angle relative to the longitudinal axis in distal direction. Further, the essentially planar area 11 is provided with a treatment aperture or window 12 through which a spatial volume 16 enclosed by the application cap 10 is in fluid communication with the atmosphere.

The electrode 9, a connecting socket (contact means) 8 and an electronics assembly (resistive element) 7 can be seen in FIG. 1 as well. These elements are arranged within the spatial volume 16 of the attachment 15 or the application cap 10 and are electrically connected or can be electrically connected to an electrical line 4, 5 within the catheter 2. Here, it is referred to the fact that the functional channels 1b-1d in the endoscope 1 are arranged around the working channel 1a so as to be off-center as a general rule. This is why an optical system of the endoscope 1 is positioned off-center, too. As the treatment window 12 is also arranged to be off-center, however, the attachment 15 can be rotated on the endoscope head with respect to the optical system in such a manner that the line of sight between the optical system and the treatment window 12 is unobstructed and indeed is not blocked by the electrode 9 protruding into the spatial volume 16.

Figure 6:
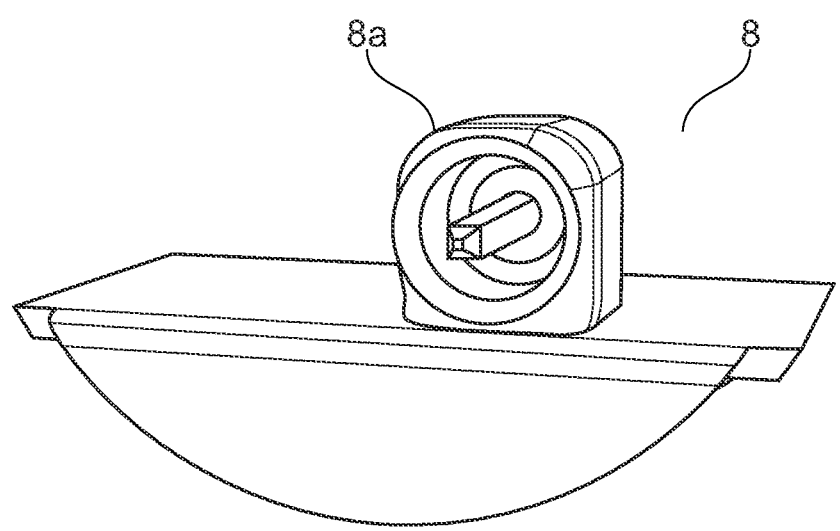
FIG. 6 shows an enlarged view of the connecting socket for making contact with the contact means (electrical conductor/cable) of a catheter placed/inserted in the endoscope and FIG. 7 shows a connector construction on the distal end of the electrical line of the catheter for connecting to the connecting socket.

In particular, a sort of mounting base (not shown in further detail) is provided within the bushing 6; a bracket-like support as it is illustrated in an enlarged view in particular in FIG. 6 can be fixed to said mounting base. The connecting socket 8 as well as the resistive element 7 (with these elements hence being able to be fixed in the bushing 6) are mounted to the support. The resistive element 7 is electrically connected to the connecting socket 8.

FIG. 2 shows a side view of the endoscope 1 and in particular its endoscope head to which the bushing 6 and, via the latter, the application cap 10 are attached. A proximal end 9a of the electrode 9 is connected to the connecting socket 8 and fixed in the bushing 6 via the support. A distal tip 9b of the electrode 9 projects into the spatial volume 16 of the attachment 15/of the application cap 10. As the affixing of the socket 8 and hence of the electrode 9 is fixed relative to the attachment 15, there will be a constructionally minimum distance between the electrode tip 9b and the treatment aperture 12.

As already explained, the mounting device/adapter/bushing 6 is made from a rubbery elastic material, for instance of silicone rubber, allowing for a flexible coupling to endoscopes 1 of different diameters. In this embodiment, the cap-shaped piece 10 is manufactured from an electrically insulating material having a predetermined rigidity (higher than that of the bushing 6), for instance a synthetic or ceramic material, which further preferably is translucent or even transparent.

Figure 4:
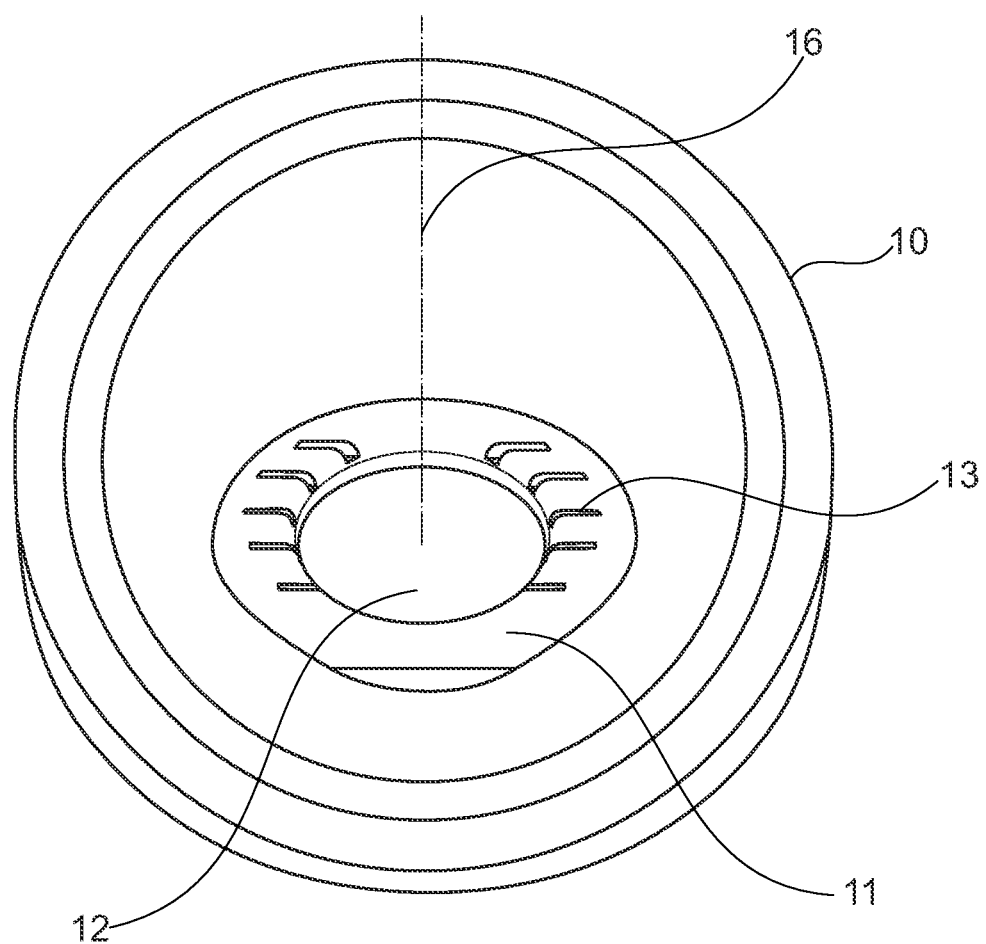
FIG. 4 shows an interior view of the attachment including the treatment aperture and in particular the scale markings/markings arranged around the treatment aperture.

Around the treatment aperture 12, in particular with reference to FIG. 4, one can see markings or scale divisions 13. These markings 13 are helpful to the user during the intervention in terms of the orientation regarding the size/dimension of the target tissue to be treated, in fact if the application cap 10 rests on the target tissue with the planar area where the treatment aperture 12 is located. The markings 13 may alternatively also be referred to as a scale or as scale markings.

Figure 3:
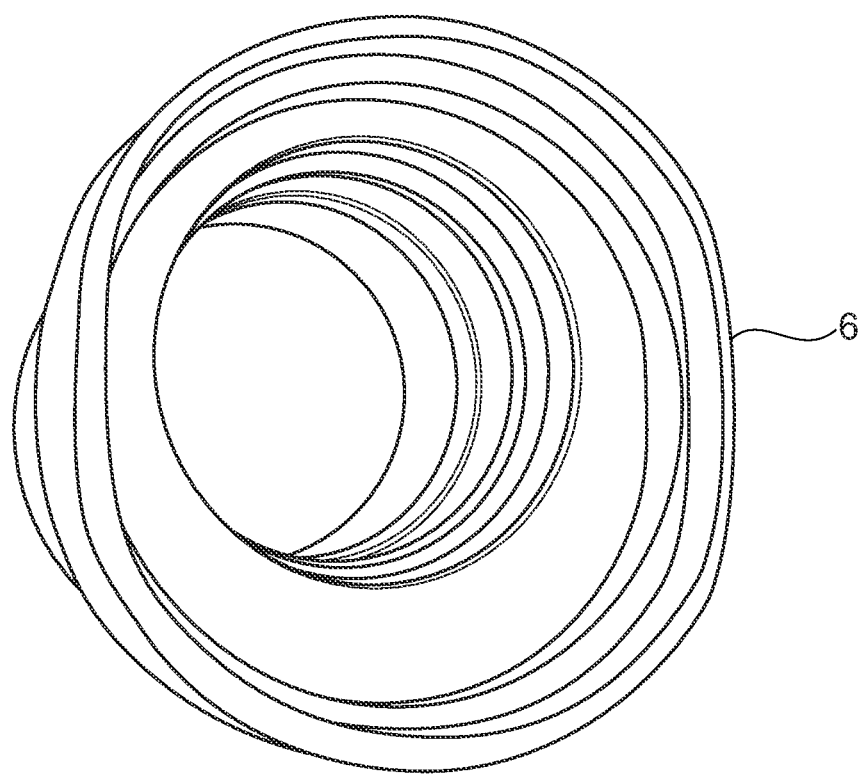
FIG. 3 shows the mounting device/adapter of the attachment in the case of a two-piece implementation of the attachment as seen from the proximal end of the cap-shaped piece.

FIG. 3 shows a perspective front view of the mounting device/adapter (bushing) 6. In the foreground, one can see the large-diameter distal end of the mounting device/adapter 6 having an internal circumferential bead, which is supposed to be coupled to the proximal end of the cap-shaped piece (application cap) 10. In this way, said mounting device/adapter/bushing 6 may optionally remain on the application cap 10 or the endoscope 1, if the attachment 15 is to be exchanged. Hence, this construction allows to mount various attachments 15 comprising different electrodes 9 or resistive elements 7, different spatial volumes 16 and/or differently dimensioned treatment apertures 12 to one and the same endoscope 1. As the resistive elements 7 are located within the attachment 15, a change of the attachment 15 allows to select different resistance values and hence differing treatment depths.

The interior view of the cap-shaped piece/cap 10 in FIG. 4 shows the treatment aperture or window 12 and the planar area 11 which ideally rests on the target tissue during treatment. Arranged around the window 12 are the previously mentioned markings or scale divisions 13. The size of these markings/scale divisions 13 is known to the treating doctor and is predetermined by design. To give an example, the distance between two scale divisions may have a specific value in mm. This is why the treating doctor is able—on an image which may be outputted by e.g. a camera, in particular an endoscope camera—to instantaneously make an exact evaluation of the size of objects which are situated within the window 12.

The electrically insulating effect of plastics and ceramics at least for the application cap 10 results in an advantageous electrical insulation of the interior space 16 of the attachment 15 with respect to the surroundings. This is why the plasma arc can have its effect only on that tissue which is visible within the area of the treatment aperture 12 (aperture area 12a), if the planar area 11 rests on the target tissue.

Figure 5:
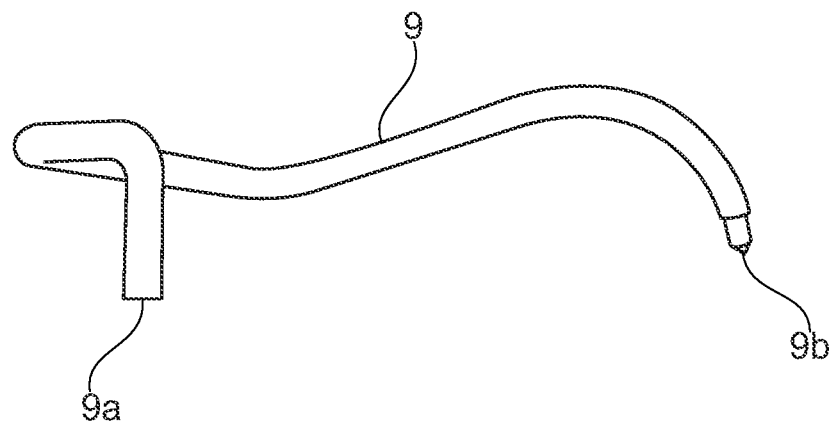
FIG. 5 shows an embodiment of the electrode.

The electrode 9 in FIG. 5 has a longitudinal extension which is curved preferably several times in order to get out of the way of the line of sight between the endoscope optics and the treatment aperture in the best possible way, and comprises a tip at its distal end 9b. The proximale end 9a of the electrode 9 is directly electrically connected to a side of the resistive element 7 (which is not visible here). The position of the electrode 9 in the attachment 15 is fixed relative to the treatment aperture 12. The electric arc is ignited between the electrode tip 9b of the electrode 9 and the target tissue which is visible through the treatment window 12.

The connecting socket 8 in FIG. 6 connects the electrical conductor 4, 5 of the catheter 2 to a side of the resistive element 7 (which is not shown here). To this end, the connecting socket comprises a housing similar to an electrical socket, in which a contact pin 8a is arranged so as to protrude into the housing. The contact pin 8a is electrically connected to the resistive element 7 which for its part is immediately connected to the electrode 9. According to FIG. 6, the socket housing is fixed to the bracket-like support, but may also be designed in one piece with it.

Figure 7:
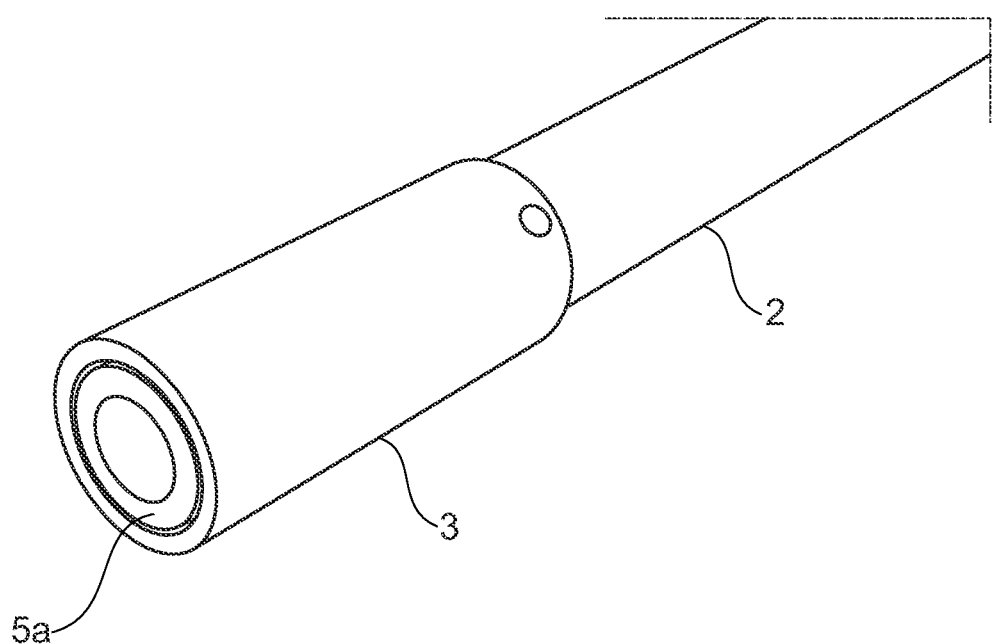

FIG. 7 shows the connection plug on the part of the electrical line of the catheter 2 in an enlarged view.

Accordingly, the catheter 2 consists of a tubular sheathing made of an electrically insulating material such as a synthetic material, a connector sleeve 3 being put on the end side of said sheathing. Arranged within the sheathing is the electrical conductor or wire 4, 5 which has its end side provided with a receiving lug 5a designed to be plugged onto the contact pin 8a. The connector sleeve 3 surrounds the circumferential side of the receiving lug 5a in a contactless manner.

In order to connect the electrode 9 to the electrical energy source, the connector sleeve 3 is plugged into the connecting socket 8 or its housing with a frictional fit or in form-locking fashion. In doing so, the receiving lug 5a is automatically put on the contact pin 8a. Finally, the bushing 6 can be put over the endoscope 1 while retracting the catheter 2 and the application cap 10 can be latched in place on the bushing 6.

The mechanical connection between the connecting socket and the plug 5a may be designed as a pure plug connection, as it has been described above. It is also possible, however, to implement it in the form of a screw- or bayonet connection.

In summary, the disclosure relates to a spacer in the form of an attachment 15 to be mounted to an endoscope 1, with the attachment 15 being designed to be cap-shaped and enclosing a spatial volume as well as being made of an insulating material. Further, the attachment 15 is equipped with a mounting device/adapter 6 designed to be coupled to a distal end of the endoscope 1. The attachment 15 has an area 11 designed to be in contact with a target tissue and further defines an aperture 12 enclosing a surface area 12a. Arranged within the spatial volume is an electrode 9 which has a distal 9b and a proximal 9a end, with the distal 9b end of the electrode 9 having a predetermined minimum distance to the closest point of the surface area 12a. Here, the closest point is that point of the surface area 12a through which a vertical line to the surface area extends which intersects the distal end of the electrode 9.

LIST OF REFERENCE NUMERALS endoscope 1
working/functional channels of the endoscope 1a-d
catheter 2
connector sleeve 3
electrical conductor 4, 5
contact lug 5a
mounting device/adapter, bushing 6
electronics assembly/resistive element 7
socket/connecting socket 8
electrode 9
electrode tip (distal end) 9a
electrode (proximal end) 9b
cap 10
tissue contact area 11
aperture/window of the cap 12
surface area 12a
markings 13
attachment 15
spatial volume 16
longitudinal axis 17

The invention claimed is:

1. A plasma-surgical instrument of the minimally invasive type, a distal end of the plasma-surgical instrument being provided with a monopolar electrode which, when supplied with electrical energy, is adapted to generate an electric arc in a specific gaseous atmosphere and with a specific distance to a target tissue, when the target tissue is placed in electrical connection with a neutral electrode, the plasma-surgical instrument comprising:

an attachment of an electrically insulating material forming a spacer, which at its distal portion surrounds a spatial volume and at its proximal portion has a mounting device or an adapter configured to be coupled to a distal end of an endoscopic feeding device for the plasma-surgical instrument, the attachment having a wall area which is designed to come into contact with the target tissue to maintain a minimum distance of the distal end of the electrode to the target tissue, wherein, the mounting device or adapter has a proximal connection opening adapted to be plugged or fitted on top of the endoscopic feeding device and the attachment forms an application cap at its distal portion surrounding the spatial volume, said application cap includes the wall area configured to contact with the target tissue, in which one single aperture with a defined surface area is formed, which is positioned and/or aligned such that the electrode protruding into the spatial volume and in particular its distal end has a predetermined minimum distance to the closest point of the surface area for the generation of the electric arc, the aperture configured and adapted to rest on the target tissue such that the spatial volume to be filled with the specific gaseous atmosphere is enclosed.

2. The plasma-surgical instrument according to claim 1, wherein the attachment is formed in two pieces and consists of a preferably thimble-shaped application cap preferably of a rigid material and the mounting device which forms a tubular bushing preferably of an elastic rubber material or is made from an adhesive tape.

3. The plasma-surgical instrument according to claim 2, wherein the mounting device has a central axis relative to which the treatment aperture is inclined at an acute angle in distal direction.

4. The plasma-surgical instrument according to claim 3, wherein the treatment aperture is arranged to be off-center with respect to the central axis.

5. The plasma-surgical instrument according to claim 2, wherein the application cap is made of an elastic rubber material.

6. The plasma-surgical instrument according to claim 2, wherein the application cap is made of an adhesive tape.

7. The plasma-surgical instrument according to claim 1, wherein the attachment has its distal end rounded in the axial direction.

8. The plasma-surgical instrument according to claim 1, wherein the electrode is fixed to the attachment while maintaining the predetermined minimum distance and can be connected, via an electrical connection means within or on the attachment, to an electrical line adapted to be pushed through the feeding device.

9. The plasma-surgical instrument according to claim 8, wherein the electrical connection means comprises a resistive element immediately upstream of the electrode and a connecting socket, for the electrical line, immediately upstream of the resistive element.

10. The plasma-surgical instrument according to claim 9, wherein the resistive element and preferably the connecting socket is mounted to the attachment and preferably to the application cap or the bushing via a common support.

11. The plasma-surgical instrument according to claim 1, wherein markings/scale divisions/a scale are/is arranged in the area of the treatment aperture facing the target tissue, said markings/scale divisions/scale during a treatment serving for evaluating the size of objects which are visible within the aperture on the target tissue.

12. The plasma-surgical instrument according to claim 1, wherein the attachment includes a temperature measuring device which is designed to measure an inside temperature of the spatial volume and to output it as processible information.

13. The plasma-surgical instrument of claim 1, wherein the closest point of the surface area is a center point of the surface area.

14. The plasma-surgical instrument of claim 1, wherein the proximal connection opening is adapted to be plugged or fitted on top of the endoscopic feeding device with functional channels of the endoscope feeding device located within the proximal connection opening.

15. The plasma-surgical instrument of claim 1, wherein the proximal connection opening is adapted to be plugged or fitted on top of the endoscopic feeding device with an optical system of the endoscope feeding device located within the proximal connection opening with an unobstructed line of sight between the optical system and the aperture.

* * * * *